(12) United States Patent
Ikeura et al.

(10) Patent No.: US 8,173,156 B2
(45) Date of Patent: May 8, 2012

(54) METHOD FOR AVOIDING CRYSTALLIZATION OF ANTI-INFLAMMATORY AGENT IN PLASTER FORMULATION

(75) Inventors: Yasuhiro Ikeura, Tosu (JP); Miyuki Shinmura, Tosu (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 46 days.

(21) Appl. No.: 12/457,410

(22) Filed: Jun. 10, 2009

(65) Prior Publication Data

US 2009/0258952 A1  Oct. 15, 2009

Related U.S. Application Data

(63) Continuation of application No. 10/258,022, filed as application No. PCT/JP2001/003283 on Apr. 17, 2001, now abandoned.

(30) Foreign Application Priority Data

Apr. 18, 2000  (JP) .............. P2000-116744

(51) Int. Cl.
*A61F 13/02* (2006.01)
*A61F 13/00* (2006.01)
*A61L 15/16* (2006.01)
*A61K 9/70* (2006.01)

(52) U.S. Cl. ............ 424/448; 424/449; 424/443

(58) Field of Classification Search ............. 424/443, 424/448, 449

See application file for complete search history.

(56) References Cited

U.S. PATENT DOCUMENTS

| | | | |
|---|---|---|---|
| 4,459,425 A | 7/1984 | Amano et al. | |
| 4,895,727 A * | 1/1990 | Allen | 424/642 |
| 4,999,379 A | 3/1991 | Fankhauser | |
| 5,059,189 A | 10/1991 | Cilento et al. | |
| 5,225,199 A | 7/1993 | Hidaka et al. | |
| 5,725,874 A | 3/1998 | Oda et al. | |
| 5,750,134 A | 5/1998 | Scholz et al. | |
| 5,866,157 A * | 2/1999 | Higo et al. | 424/448 |
| 5,869,087 A * | 2/1999 | Hirano et al. | 424/449 |
| 6,143,319 A * | 11/2000 | Meconi et al. | 424/448 |
| 6,914,169 B1 | 7/2005 | Oota et al. | |
| 2003/0109819 A1 | 6/2003 | Tsuruda et al. | |
| 2003/0138479 A1 | 7/2003 | Mizota et al. | |

FOREIGN PATENT DOCUMENTS

| | | |
|---|---|---|
| CA | 2 304 784 A | 4/1999 |
| EP | 0 607 434 A1 | 7/1994 |
| EP | 0 760 238 A1 | 3/1997 |

(Continued)

OTHER PUBLICATIONS

Hawley Condenced chemical dictionary, fourteenth edition.*

(Continued)

*Primary Examiner* — Isis Ghali
(74) *Attorney, Agent, or Firm* — The Nath Law Group

(57) ABSTRACT

An anti-inflammatory-containing plaster is provided. The anti-inflammatory-containing plaster may include, e.g., a styrene-isoprene-styrene block copolymer, a high molecular weight polyisobutylene, a low molecular weight polyisobutylene, a tackifier, a plasticizer, a dispersant, and an anti-inflammatory having a carboxyl group or a salt thereof. However, the anti-inflammatory-containing plaster does not contain L-menthol. The anti-inflammatory-containing plaster has medicament release rates of 20-64% by mass and 40-93% by mass at one hour and three hours, respectively.

9 Claims, 1 Drawing Sheet

FOREIGN PATENT DOCUMENTS

| | | |
|---|---|---|
| EP | 0 781 553 A1 | 7/1997 |
| EP | 0 968 712 A1 | 1/2000 |
| EP | 1 238 664 A1 | 9/2002 |
| EP | 1 284 138 A1 | 2/2003 |
| EP | 1 293 199 A1 | 3/2003 |
| JP | 59051215 A | 3/1984 |
| JP | 64040420 A | 2/1989 |
| JP | 5-501261 A | 3/1993 |
| JP | 05-331064 A | 12/1993 |
| JP | 2816765 | 8/1998 |
| WO | WO 91/06290 A1 | 5/1991 |
| WO | WO 98/24423 A1 | 6/1998 |

OTHER PUBLICATIONS

Office Action issued on Jun. 28, 2011, in counterpart Japanese Patent Application No. 2001-575991.

* cited by examiner

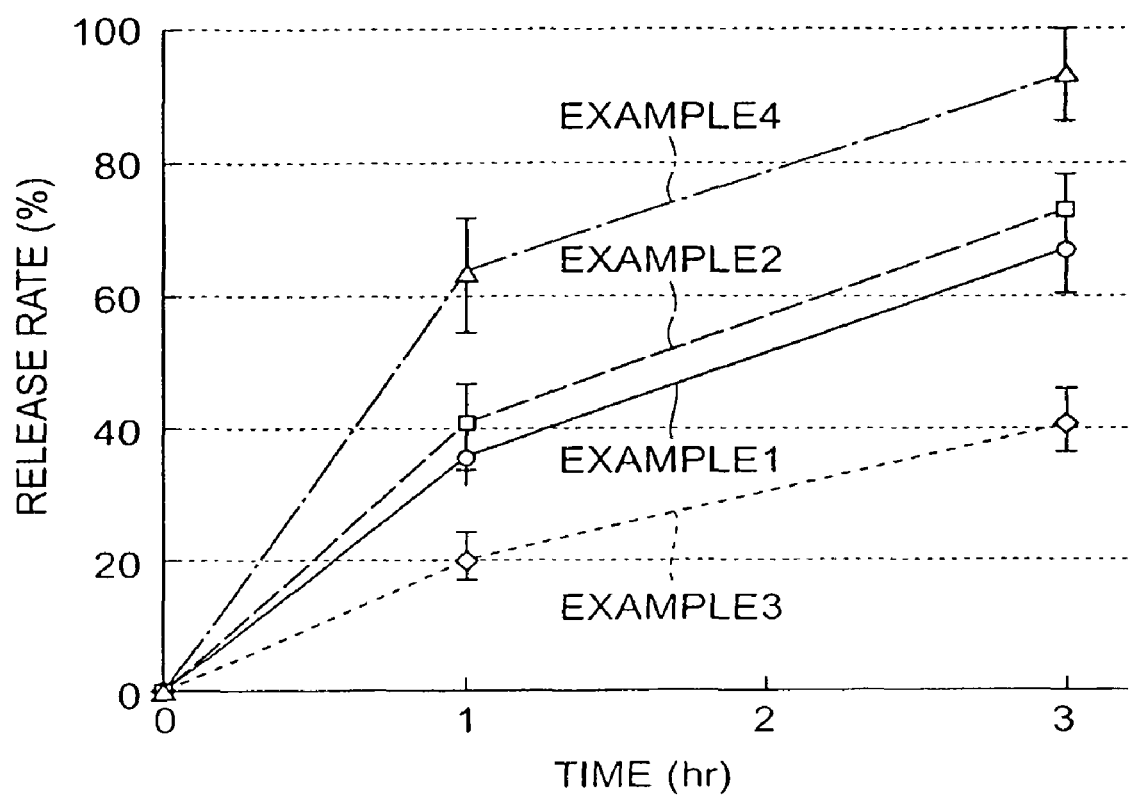

METHOD FOR AVOIDING CRYSTALLIZATION OF ANTI-INFLAMMATORY AGENT IN PLASTER FORMULATION

This is a Continuation Application of U.S. patent application Ser. No. 10/258,022, filed on Oct. 18, 2002, which was filed under 35 U.S.C. 371 as a national stage of PCT/JP01/03283, filed on Apr. 17, 2001, the entire content of each of which is hereby incorporated herein by reference in its entirety.

TECHNICAL FIELD

This invention relates to antiinflammatory-containing plasters for percutaneous administration that are intended for anti-inflammatory, analgesic effect. More specifically, it relates to an antiinflammatory-containing plaster comprising as the medicinally effective component, an antiinflammatory having a carboxyl group or a salt thereof and which is intended for the treatment of lumbago, muscle ache and periarthritis.

Background Art

A number of preparations for percutaneous administration are known for non-steroidal antiinflammatories that are intended for absorption through skin; plasters are also known that utilize the base comprising a thermoplastic elastomer such as natural rubber, an acrylic acid polymer, or a styrene-isoprene-styrene block copolymer. Specifically, Japanese Patent No. 2,816,765 (Official Gazette) proposes a plaster where an antiinflammatory belonging to the carboxylic acid type is blended with a base comprising a styrene-isoprene-styrene block copolymer and polyisobutylene (both as base polymer), a rosin ester derivative and L-menthol (both as solubilizer), and liquid paraffin (as plasticizer). Also, International Publication WO96/08245 (Official Gazette) proposes a plaster where an antiinflammatory having a carboxylic acid group within its molecule in addition to an esterification retardant, which is a metal salt of fatty acid, for preventing the esterification between the antiinflammatory having a carboxylic acid group and L-menthol is blended with a styrene-isoprene-styrene block copolymer and polyisobutylene (both as base polymer), L-menthol (as solubilizer), a rosin ester derivative (as tackifier), and liquid paraffin (as plasticizer).

DISCLOSURE OF THE INVENTION

The present inventors, however, found that the anti-inflammatory, analgesic plasters in the prior art as disclosed in Japanese Patent No. 2,816,765 and International Publication WO96/08245 are still unsatisfactory, as will be described below. Specifically, in the anti-inflammatory, analgesic plasters in the prior art when such an antiinflammatory having a carboxyl group and L-menthol were combined for use, the antiinflammatory and L-menthol experienced partial esterification by being left for a long period of time at the preparation-forming step or in the preparation; and the reaction was not necessarily prevented to sufficient degree even when the metal salt of fatty acid was blended as the esterification retardant. Some people also try to avoid applying the plaster because the plaster vaporizes the smell of L-menthol to the environment due to sublimability when it contains L-menthol.

Separately, L-menthol acts as a solubilizer to an antiinflammatory having a carboxyl group. For this reason, when no L-menthol is blended with the plaster in the prior art containing the antiinflammatory having a carboxyl group, it will be difficult to stably maintain the constantly high medicament release, which is unsatisfactory from the standpoints of duration of pharmacological effects (anti-inflammatory, analgesic effect) and others.

This invention has been made in view of the problems that are inherent in the aforementioned prior art. An object of the invention is to provide an antiinflammatory-containing plaster that can consistently produce, over a long period of time, a sufficient anti-inflammatory, analgesic effect by the antiinflammatory having a carboxyl group or a salt thereof without bringing harmful effects such as skin irritation and that is excellent in the stability of adhesive base as well as in its adhesion with alleviated pain upon peeling despite the fact that L-menthol is not blended therein.

The present inventors diligently conducted intensive research in order to achieve the above-stated object. Consequently, the inventors found that an antiinflammatory-containing plaster can be obtained where the release rates of its medicinally effective component, the antiinflammatory, one hour and three hours later are in a predetermined range and which can produce a sufficient antiinflammatory, analgesic effect consistently over a long period of time without bringing harmful effects and which also has excellent stability of the adhesive base by including specific components in specific proportions into the plaster without combining the antiinflammatory having a carboxyl group or a salt thereof with L-menthol; the inventors have thus arrived at this invention.

Specifically, an antiinflammatory-containing plaster of this invention comprises 5-40% by mass of a styrene-isoprene-styrene block copolymer, 1-25% by mass of a high molecular weight polyisobutylene, 0.5-24% by mass of a low molecular weight polyisobutylene, 3-50% by mass of a tackifier, 20-70% by mass of a plasticizer, 0.01-7% by mass of a dispersant, and 0.1-8% by mass of an antiinflammatory having a carboxyl group or a salt thereof as the medicament, but which contains no L-menthol.

In the antiinflammatory-containing plaster of this invention described above, it is preferred that the medicament release rate at one hour after the start of test is 20-64% by mass and the medicament release rate at three hours after the start of test is 40-93% by mass when the water-releasing test using a rotating cylinder described in the release test as prescribed in United State Pharmacopoeia is carried out under the following conditions:

Test solution: distilled water
Solution temperature: 32±0.5° c.
The distance between the lower end of cylinder and the inner bottom surface of container: 12±2 mm
The number of revolutions: 50 rpm.

Preferably, the tackifier is a rosin-based resin; the plasticizer is liquid paraffin; and the dispersant is a metal salt of stearic acid.

Further, the antiinflammatory having a carboxyl group or a salt thereof used in the antiinflammatory-containing plaster of this invention is preferably at least one member antiinflammatory selected from the group consisting of indomethacin, ketoprofen, flurbiprofen, diclofenac, loxoprofen, ketorolac, and the salts of the foregoing.

BRIEF DESCRIPTION OF THE DRAWINGS

FIG. 1 is a graph showing the results of medicament release test.

BEST MODE FOR CARRYING OUT THE INVENTION

The antiinflammatory-containing plaster of this invention comprises as the medicinally effective component, an antiinflammatory having a carboxyl group or a salt thereof. Such antiinflammatories include the antiinflammatories having a carboxyl group (carboxylic acid group) such as indomethacin, ketoprofen, flurbiprofen, diclofenac, loxoprofen, and ketorolac as well as the antiinflammatories where the hydrogen atom of the carboxyl group has been substituted by a medically acceptable salt such as an inorganic salt (e.g., sodium salt, potassium salt, calcium salt, or ammonium salt) or an organic salt (e.g., tromethamine salt). Preferred among those mentioned are indomethacin, ketoprofen, flurbiprofen, diclofenac sodium, diclofenac ammonium, loxoprofen sodium, and ketorolac tromethamine.

The blending proportion of the antiinflammatory having a carboxyl group or a salt thereof in the plaster of this invention is 0.1-8% by mass, preferably 0.5-5% by mass. By employing this blending proportion, good transdermal absorption of the medicament, duration of efficacy, dispersability of the medicament and so on, besides being economically outstanding, will be achieved. Here, if the blending proportion of the antiinflammatory is less than 0.1% by mass, sufficient efficacy will not be attained. On the other hand, if the blending proportion exceeds 8% by mass, it will not be suitable from the standpoints of the occurrence of harmful effects such as skin irritation caused by excessive administration and economical efficiency.

The antiinflammatory-containing plaster of this invention does not contain L-menthol that acts as solubilizer to the antiinflammatory having a carboxyl group or a salt thereof. Accordingly, in the antiinflammatory-containing plaster of this invention, the esterification of the antiinflammatory is fully prevented and antiinflammatory, analgesic effect by the antiinflammatory can be consistently produced over a long period of time without bringing harmful effects such as skin irritation by including specific components in specific proportions into the plaster (as will be described hereafter), despite the fact that L-menthol, which acts as solubilizer, is not contained in the plaster.

Moreover, the antiinflammatory-containing plaster of this invention is such that desirably the medicament release rate at one hour after the start of test is 20-70% by mass (preferably 30-65% by mass) and the medicament release rate at three hours after the start of test is 40-93% by mass (preferably 60-90% by mass) when the water-releasing test using a rotating cylinder described in the release test as prescribed in United State Pharmacopoeia is carried out under the following conditions:

Test solution: distilled water
  Solution temperature: 32±0.5° c.
  The distance between the lower end of cylinder and the inner bottom surface of container: 12±2 mm
  The number of revolutions: 50 rpm.

If the medicament release rate is below the lower limit of the above-mentioned range, sufficient efficacy will not be attained. On the other hand, if it exceeds the upper range, that will raise concern for bringing harmful effects such as skin irritation caused by excessive administration of the medicament. Accordingly, the antiinflammatory-containing plaster of this invention, which is able to stably maintain such constantly high medicament release, has for the first time made it possible to provide a drug that consistently produces an excellent therapeutic effect over a long period of time without bringing harmful effects such as skin irritation upon administration.

The antiinflammatory-containing plaster of this invention may be obtained by including as the medicinally effective component, an antiinflammatory having a carboxyl group or a salt thereof in a specific blending proportion into a base comprising a styrene-isoprene-styrene block copolymer, a high molecular weight isobutylene, a low molecular weight isobutylene, a tackifier, a plasticizer, and a dispersant, respectively, in specific blending proportions, but which contains no L-menthol. Various base components used for forming the plaster of the invention will be described in detail hereafter.

The styrene-isoprene-styrene block copolymer according to this invention is a block copolymer of styrene and isoprene and is provided with polystyrene at both ends thereof. Such styrene-isoprene-styrene block copolymers include, among others, Cariflex TR-1101, TR-1107 and Cariflex TR-1111 (trade names, available from Shell Kagaku K.K.); JSR5000 and JSR5002 (trade names, available from Japan Synthetic Rubber Co., Ltd.); Quintac 3530, 3421 and 3570C (trade names, available from Nippon Zeon Co., Ltd.); Kraton D-KX401CS and D-1107CU (trade names, available from Shell Kagaku K.K.); and Solprene 428 (trade name, available from Phillips Petroleum International, Ltd.). One kind or a combination of two or more kinds of the foregoing may be used.

The blending proportion of the styrene-isoprene-styrene block copolymer is 5-40% by mass, preferably 8-35% by mass, and more preferably 10-30% by mass based on the total weight of the plaster (adhesive preparation). If the blending proportion is less than 5% by mass, the cohesive force of the base will decrease and the shape retention of the base will degrade. On the other hand, if it exceeds 40% by mass, the cohesive force of the base will increase, thus likely resulting in a reduction in adhesive strength and lowering workability.

The high molecular weight polyisobutylene according to this invention is a polymer of isobutylene, preferably with an average molecular weight of 50,000-200,000. As such high molecular weight polyisobutylene, there are mentioned: Oppanol 80, 100, 120, 150, and 200 (trade names, available from BASF AG); and Vistanex MM L-80, MM L-100, MM L-120, MM L-140 (trade names, available from Exxon Chemical Japan Ltd.). One kind or a combination of two or more kinds of the foregoing may be used.

The blending proportion of the high molecular weight polyisobutylene is 1-25% by mass, preferably 2-18% by mass, and more preferably 3.6-12% by mass based on the total weight of the plaster (adhesive preparation). If the blending proportion is less than 1% by mass, the shape retention of the base will degrade during prolonged storage, exudation will tend to appear, and the releasing-capability of the antiinflammatory will likely decrease. On the other hand, if it exceeds 25% by mass, the releasing-capability of the antiinflammatory will also likely decrease.

The low molecular weight polyisobutylene according to this invention is a polymer of isobutylene, preferably with an average molecular weight of 5,000-15,000. As such low molecular weight polyisobutylene, there are mentioned: Oppanol 10, 12, 12SF, 15, 15SF, 30SF, 50, 50SF (trade names, available from BASF AG); and Vistanex LM-MS, LM-MH, LM-H (trade names, available from Exxon Chemical Japan Ltd.). One kind or a combination of two or more kinds of the foregoing may be used.

The blending proportion of the low molecular weight polyisobutylene is 0.5-24% by mass, preferably 1-20% by mass, and more preferably 2-15% by mass based on the total weight of the plaster (adhesive preparation). If the blending proportion is less than 0.5% by mass, degradation of the adhesive properties will occur to easily cause peeling during affixing and the releasing-capability of the antiinflammatory will also likely decrease. On the other hand, if it exceeds 24% by mass, the adhesive properties will excessively increase, thus likely resulting in rash or pain upon peeling.

The tackifier according to this invention is preferably a rosin-based resin made from rosin or a rosin derivative as a base material; and a rosin ester, a hydrogenated rosin ester, a maleic acid-modified rosin ester, or the like may preferably be used. Such tackifiers (rosin-based resins) include, among others, Hariester L, S and P (trade names, available from Harima Chemicals, Inc.); Super Ester A-75 and S-100, Pinecrystal KE-100 and KE-311, Ester Gum A, AA-G, H and HP (trade names, available from Arakawa Chemical Industries, Ltd.); Hercolyn D, Foral 85, 100 and 105 (trade names, available from Rika-Hercules Inc.). One kind or a combination of two or more kinds of the foregoing may be used.

The blending proportion of the tackifier is 3-50% by mass, preferably 4-40% by mass, and more preferably 5-30% by mass based on the total weight of the plaster (adhesive preparation). If the blending proportion is less than 3% by mass, degradation of the adhesive properties and crystallization of the antiinflammatory will occur to easily cause peeling during affixing, and the releasing-capability of the antiinflammatory will also likely decrease. On the other hand, if it exceeds 50% by mass, the adhesive properties and dissolution of the antiinflammatory will tend to increase, thus likely resulting in rash or pain upon peeling as well as in lowered medicament releasing-capability.

The plasticizer according to this invention is an agent compatible with the other base components and capable of providing the base with flexibility. Almond oil, olive oil, camellia oil, persic oil, peanut oil, liquid paraffin, and the like may preferably be used. One kind, or two or more kinds of these plasticizers may be used and among them, the liquid paraffin is particularly preferred.

The blending proportion of the plasticizer is 20-70% by mass, preferably 25-65% by mass, and more preferably 30-60% by mass based on the total weight of the plaster (adhesive preparation). If the blending proportion is less than 20% by mass, poor plasticity will result to likely lower adhesive properties and productivity. On the other hand, if it exceeds 70% by mass, the adhesive preparation will be too soft, likely causing the occurrence of cohesion failure of the base.

In the antiinflammatory-containing plaster of this invention, a dispersing agent is further included in a specific blending proportion in the base containing the styrene-isoprene-styrene block copolymer, the high molecular weight polyisobutylene, the low molecular weight polyisobutylene, the tackifier, and the plasticizer as described above. The dispersing agent according to the invention is an agent capable of enhancing dispersibility of different components in the preparation, particularly those of the styrene-isoprene-styrene block copolymer and the high molecular weight- and low molecular weight-polyisobutylenes. Synthetic aluminum silicate, hydrated aluminum silicate, aluminum hydroxide, magnesium silicate, zinc oxide, titanium oxide, metal salts of fatty acid such as metal salts of stearic acid may be used. One kind, or two or more kinds of these dispersing agents may be used and among them, the metal salts of stearic acid (e.g., zinc stearate, calcium stearate, aluminum stearate, and magnesium stearate) are preferred: zinc stearate is especially preferred.

The blending proportion of the dispersing agent is 0.01-7% by mass, preferably 0.05-6% by mass, and more preferably 0.1-5% by mass, based on the total weight of the plaster (adhesive preparation). If the blending proportion is less than 0.01% by mass, the dispersibility of the high molecular weight polyisobutylene and the diffusibility of the antiinflammatory in the base will be poor, resulting in the lowered releasing-capability of the antiinflammatory. On the other hand, if it exceeds 7% by mass, the dispersant itself will leak to lower adhesive properties and to likely cause peeling during affixing.

In the plaster of this invention, an antiinflammatory having a carboxyl group or a salt thereof as the medicinally effective component is contained in the above-mentioned base in a 0.1-8% by mass proportion as described above.

Because the above-stated different components, particularly the high molecular weight polyisobutylene, the low molecular weight polyisobutylene, and the dispersing agent, are contained in the plaster of this invention having the above-stated composition, various components (particularly, the styrene-isoprene-styrene block copolymer and polyisobutylenes) are uniformly dispersed in the preparation without cohesion and the uniform dispersibility of the antiinflammatory is adequately maintained. This will stably sustain the constantly high medicament release in the plaster of this invention despite the fact that it contains no L-menthol which would serve to dissolve the antiinflammatory. Thus, the sufficient anti-inflammatory, analgesic effect by the antiinflammatory will be consistently produced over a long period of time without bringing harmful effects such as skin irritation. Besides, the excellent stability of the adhesive base and adhesion of preparations as well as alleviated pain upon peeling can be realized.

The plaster of this invention may further contain, as necessary, other additive components such as an antioxidant, a filler, a crosslinking agent, a preservative, an ultraviolet light absorber, and an absorption enhancer in addition to the styrene-isoprene-styrene block copolymer, the high molecular weight polyisobutylene, the low molecular weight polyisobutylene, the tackifier, the plasticizer, the dispersant, and the antiinflammatory as described above. The blending proportion of the other additive components is not particularly limited, but is preferably 0.01-7% by mass, and more preferably 0.1-5% by mass based on the total weight of the plaster (adhesive preparation).

Preferred as such a antioxidant are tocopherol, tocopherol derivatives, ascorbic acid, esters of ascorbic acid and stearic acid, nordihydroguaiaretic acid, dibutylhydroxytoluene, butylhydroxyanisole and the like. Also preferred as the filler are calcium carbonate, magnesium carbonate, silicates (e.g., aluminum silicate and magnesium silicate), silicic acid, barium sulfate, calcium sulfate, calcium zincate, zinc oxide, titanium oxide, and the like. In addition, preferred as the crosslinking agent are organic crosslinkers including thermo-setting resins (e.g., amino resin, phenol resin, epoxy resin, alkyd resin, and unsaturated polyester), isocyanates, and blocked isocyanates and inorganic crosslinkers such as metals or metal compounds.

Further, preferred as the preservative are ethyl paraben, propyl paraben, butyl paraben, and the like. Still further preferred as the ultraviolet light absorber are p-aminobenzoic acid derivatives, anthranilic acid derivatives, salicylic acid derivatives, coumarin derivatives, amino acid derivatives, imidazoline derivatives, pyridine derivatives, and dioxane derivatives. The absorption enhancers include, among others, terpene oils such as d-limonene, esters of fatty acid (e.g., glycerol monolaurate, glycerol monooleate, and diethyl sebacate), azone, azacycloalkanes such as 1-[2-(decylthio)ethyl] azacyclopentan-2-one, and higher fatty acids such as oleic acid, lauric acid, and myristic acid.

The thickness (not including thickness of a backing and a released liner as described hereafter) of the plaster (i.e., the plaster layer) of this invention prepared using the various components is preferably 50-300 µm and more preferably 80-200 µm. Here, if the thickness is less than 50 µm, the duration of adhesiveness and adhesion will tend to decrease. On the other hand, if it exceeds 300 µm, the cohesive force will tend to decrease and the shape retention will tend to degrade.

Because of the use of a highly flexible backing as described below, the plaster of this invention freely expands and contracts longitudinally and laterally, thus achieving the affixing feeling at high level. In other words, according to the antiinflammatory-containing plaster of this invention, it becomes possible to employ a backing with flexibility, and adhesion will be realized such that the plaster can be affixed even to a flexion site like elbow or knee with adequate compatibility and without being peeled off over a long period of time.

The backing of plaster of this invention is desirably one that does not affect release of the medicament from the plaster of the invention; and flexible or non-flexible materials may be used. Usable backings for the invention include, among others, a film, a sheet, a sheet porous body, a sheet foam, and a woven or non-woven fabric of a synthetic resin such as polyethylene, polypropylene, polybutadien, an ethylene-vinyl acetate copolymer, polyvinyl chloride, a polyester, nylon, or a polyurethane; paper; fabric; non-woven fabric; and a laminated product of the foregoing.

Among these plaster backings, a backing with flexibility is preferred. Its load at 30%-elongation (modulus) (as set forth in JIS L 1096) is preferably 100-800 g longitudinally (lengthwise) and 500-2500 g laterally (widthwise), more preferably 100-500 g longitudinally and 500-2000 g laterally, under such measurement conditions that the sample width is 50 mm, the sample length 200 mm, and the elongation speed is 200 mm/min. Also, its recovery factor at 50%-elongation (as set forth in JIS L 1096) is preferably 75-95% longitudinally and 65-85% laterally, more preferably 80-95% longitudinally and 70-85% laterally, under such measurement conditions that the sample width is 50 mm, the sample length is 200 mm, and the elongation speed is 200 mm/min. If the load at 30%-elongation for these backings is below the lower limit, the backing will lose its sturdiness when affixed and handling tends to be difficult. On the other hand, if it exceeds the upper limit, adhesion to the flexion site over a long period of time tends to be difficult. Further, if the recovery factor at 50%-elongation for those backings is below the lower limit, compatibility with the flexion site (when affixed thereto) will be poor and satisfactory adhesion is not likely to be attained. On the other hand, if it exceeds the upper limit, handling tends to be difficult upon affixing.

As described above, the plaster of this invention, through the use of a highly flexible backing, can firmly be affixed to flexion sites with vigorous movement such as elbow and knee. Furthermore, the basic weight (weight per unit area) of the backing according to the invention is preferably 100±30 g/m².

A preferred example of the method for preparing the antiinflammatory-containing plaster of this invention will next be described.

First, the styrene-isoprene-styrene block copolymer, the high molecular weight polyisobutylene, the low molecular weight polyisobutylene, the tackifier, the plasticizer, the dispersing agent, and any components (when other additive components, except for the oxidant and the absorption enhancer, are to be included) are blended at the respectively predetermined proportions to yield a mixture, and the mixture is heated and stirred under an inert atmosphere of nitrogen or the like to yield a dissolved material. The temperature upon stirring is preferably 110-200° C. and the stirring time is preferably 30-120 minutes. Subsequently, the antiinflammatory (the medicinally effective component), together with any antioxidant or absorption enhancer if it is to be included, is added to the aforementioned dissolved material and the mixture is then stirred preferably at 110-200° C. and preferably for 5-30 minutes, thereby yielding a uniformly dissolved material. Also, the various components described above may be added to an organic solvent such as hexane or toluene or ethyl acetate so as to give their predetermined proportions, and may be stirred to yield a uniformly dissolved material.

Next, this dissolved material is spread directly over the backing by an ordinary method, and then it is cut into desired shapes after being covered with a released liner (peeled cover). Alternatively, once this dissolved material has been spread over the released liner, it is allowed to cover the backing and after the dissolved material is pressed and transferred onto the backing, it may be cut into desired shapes. When a uniformly dissolved material has been obtained using an organic solvent, it is dried with a dryer, after having been spread over the backing, and the organic solvent is removed by evaporation, after which the dissolved material may be covered with a released liner; or alternatively, after which the dissolved material may preferably be pressed and transferred onto the backing. Such released liners include, among others, a released paper processed by release treatment (treatment for facilitating release); cellophane; and a synthetic resin film of polyethylene, polypropylene, polyester, or the like.

It should be noted that only one embodiment has been described with respect to the order of blending the respective base components, the medicinally effective component, and the other additive components in the above preparation method and that the preparation method for the plasters of this invention is not limited to this method relying on the particular blending order.

EXAMPLES

The plasters containing an antiinflammatory of this invention will be described in more detail by way of examples and comparative examples; however, they are not to be limited to those described in the following examples. In the examples and comparative examples, "part(s)" mean "part(s) by mass" unless otherwise stated specifically.

Example 1

| | |
|---|---|
| styrene-isoprene-styrene block copolymer (Cariflex TR-1111) | 20.00 parts |
| high molecular weight polyisobutylene (Vistanex MM L-120) | 5.00 parts |
| low molecular weight polyisobutylene (Vistanex LM-H) | 5.00 parts |
| rosin-based resin (Pinecrystal KE-311) | 16.00 parts |
| liquid paraffin | 51.90 parts |
| zinc stearate | 0.10 parts |
| ketoprofen | 2.00 parts |

A plaster was prepared in the formulation described above according to the aforementioned preparation method. Specifically, the components other than the antiinflammatory in the formulation described above were blended to yield a mixture and the mixture was heated and stirred under the nitrogen atmosphere to yield a dissolved material. Subsequently, the antiinflammatory, which was the medicinally effective component, was added to the dissolved material and the mixture was heated and stirred to yield a uniformly dissolved material. Then, this dissolved material was spread over a backing (non-woven fabric of polypropylene) so that the thickness of the plaster layer obtained was 150 μm. Thereafter, the dissolved material was covered with a released liner (polyester film) and the product after having been cooled was cut into the desired dimension, whereby the antiinflammatory-containing plaster was obtained. The backing used here was one of which the load at 30%-elongation was 250 g longitudinally and 1200 g laterally and the recovery factor at 50%-elongation was 90% longitudinally and 75% laterally.

Example 2

| | |
|---|---|
| styrene-isoprene-styrene block copolymer (Cariflex TR-1111) | 20.00 parts |
| high molecular weight polyisobutylene (Vistanex MM L-120) | 5.00 parts |
| low molecular weight polyisobutylene (Vistanex LM-H) | 5.00 parts |
| rosin-based resin (Pinecrystal KE-311) | 16.00 parts |
| liquid paraffin | 50.00 parts |
| zinc stearate | 2.00 parts |
| ketoprofen | 2.00 parts |

A plaster was prepared similarly to Example 1, except that it was formulated as described above.

Example 3

| | |
|---|---|
| styrene-isoprene-styrene block copolymer (Cariflex TR-1111) | 20.00 parts |
| high molecular weight polyisobutylene (Vistanex MM L-120) | 5.00 parts |
| low molecular weight polyisobutylene (Vistanex LM-H) | 5.00 parts |
| rosin-based resin (Pinecrystal KE-311) | 16.00 parts |
| liquid paraffin | 51.95 parts |
| zinc stearate | 0.05 parts |
| ketoprofen | 2.00 parts |

A plaster was prepared similarly to Example 1, except that it was formulated as described above.

Example 4

| | |
|---|---|
| styrene-isoprene-styrene block copolymer (Cariflex TR-1111) | 20.00 parts |
| high molecular weight polyisobutylene (Vistanex MM L-120) | 5.00 parts |
| low molecular weight polyisobutylene (Vistanex LM-H) | 5.00 parts |
| rosin-based resin (Pinecrystal KE-311) | 16.00 parts |
| liquid paraffin | 46.00 parts |
| zinc stearate | 6.00 parts |
| ketoprofen | 2.00 parts |

A plaster was prepared similarly to Example 1, except that it was formulated as described above.

Example 5

| | |
|---|---|
| styrene-isoprene-styrene block copolymer (Cariflex TR-1111) | 20.00 parts |
| high molecular weight polyisobutylene (Vistanex MM L-120) | 3.00 parts |
| low molecular weight polyisobutylene (Vistanex LM-H) | 5.00 parts |
| rosin-based resin (Pinecrystal KE-311) | 16.00 parts |
| liquid paraffin | 53.90 parts |
| zinc stearate | 0.10 parts |
| ketoprofen | 2.00 parts |

A plaster was prepared similarly to Example 1, except that it was formulated as described above.

Example 6

| | |
|---|---|
| styrene-isoprene-styrene block copolymer (Cariflex TR-1111) | 20.00 parts |
| high molecular weight polyisobutylene (Vistanex MM L-120) | 25.00 parts |
| low molecular weight polyisobutylene (Vistanex LM-H) | 5.00 parts |
| rosin-based resin (Pinecrystal KE-311) | 16.00 parts |
| liquid paraffin | 30.00 parts |
| zinc stearate | 2.00 parts |
| diclofenac sodium | 2.00 parts |

A plaster was prepared similarly to Example 1, except that it was formulated as described above.

Example 7

| | |
|---|---|
| styrene-isoprene-styrene block copolymer (Cariflex TR-1101) | 10.00 parts |
| high molecular weight polyisobutylene (Oppanol 80) | 3.60 parts |
| low molecular weight polyisobutylene (Vistanex LM-MS) | 20.00 parts |
| rosin-based resin (Pinecrystal KE-100) | 15.80 parts |
| liquid paraffin | 50.00 parts |
| zinc stearate | 0.10 parts |
| indomethacin | 0.50 parts |

A plaster was prepared similarly to Example 1, except that it was formulated as described above.

Example 8

| | |
|---|---|
| styrene-isoprene-styrene block copolymer (Cariflex TR-1111) | 20.00 parts |
| high molecular weight polyisobutylene (Oppanol 120) | 20.00 parts |
| low molecular weight polyisobutylene (Oppanol 15) | 17.00 parts |
| rosin-based resin (Ester Gum A) | 5.00 parts |
| liquid paraffin | 30.00 parts |
| zinc stearate | 5.00 parts |
| ketoprofen | 3.00 parts |

A plaster was prepared similarly to Example 1, except that it was formulated as described above.

Example 9

| | |
|---|---|
| styrene-isoprene-styrene block copolymer (JSR 5000) | 30.00 parts |
| high molecular weight polyisobutylene (Vistanex MM L-80) | 5.00 parts |
| low molecular weight polyisobutylene (Vistanex LM-MH) | 1.00 parts |
| rosin-based resin (Foral 85) | 30.00 parts |
| liquid paraffin | 33.40 parts |
| aluminum silicate | 0.10 parts |
| indomethacin | 0.50 parts |

A plaster was prepared similarly to Example 1, except that it was formulated as described above.

Example 10

| | |
|---|---|
| styrene-isoprene-styrene block copolymer (JSR 5002) | 10.00 parts |
| high molecular weight polyisobutylene (Vistanex MM L-100) | 5.00 parts |
| low molecular weight polyisobutylene (Vistanex LM-MS) | 5.00 parts |
| rosin-based resin (Foral 100) | 9.90 parts |
| liquid paraffin | 65.00 parts |
| aluminum hydroxide | 0.10 parts |
| flurbiprofen | 5.00 parts |

A plaster was prepared similarly to Example 1, except that it was formulated as described above.

Comparative Example 1

| | |
|---|---|
| styrene-isoprene-styrene block copolymer (Cariflex TR-1111) | 20.00 parts |
| high molecular weight polyisobutylene (Vistanex MM L-120) | 5.00 parts |
| low molecular weight polyisobutylene (Vistanex LM-H) | 5.00 parts |
| rosin-based resin (Pinecrystal KE-311) | 16.00 parts |
| liquid paraffin | 48.00 parts |
| zinc stearate | 2.00 parts |
| ketoprofen | 2.00 parts |
| L-menthol | 2.00 parts |

A plaster was prepared similarly to Example 1, except that it was formulated as described above and L-menthol and the antiinflammatory were together added to the dissolved material.

Comparative Example 2

| | |
|---|---|
| styrene-isoprene-styrene block copolymer (Cariflex TR-1111) | 25.00 parts |
| rosin-based resin (Pinecrystal KE-311) | 5.00 parts |
| liquid paraffin | 68.00 parts |
| ketoprofen | 0.50 parts |
| L-menthol | 1.50 parts |

A plaster was prepared similarly to Example 1, except that it was formulated as described above and L-menthol and the antiinflammatory were together added to the dissolved material.

Comparative Example 3

| | |
|---|---|
| styrene-isoprene-styrene block copolymer (Cariflex TR-1111) | 15.00 parts |
| high molecular weight polyisobutylene (Vistanex MM L-120) | 5.00 parts |
| rosin-based resin (Pinecrystal KE-311) | 40.00 parts |
| liquid paraffin | 23.00 parts |
| ketoprofen | 5.00 parts |
| L-menthol | 10.00 parts |
| butylhydroxytoluene | 2.00 parts |

A plaster was prepared similarly to Example 1, except that it was formulated as described above and L-menthol, butylhydroxytoluene, and the antiinflammatory were together added to the dissolved material.

Comparative Example 4

| | |
|---|---|
| styrene-isoprene-styrene block copolymer (Cariflex TR-1111) | 24.00 parts |
| rosin-based resin (Pinecrystal KE-311) | 5.00 parts |
| liquid paraffin | 68.00 parts |
| zinc stearate | 1.00 parts |
| ketoprofen | 0.50 parts |
| L-menthol | 1.50 parts |

A plaster was prepared similarly to Example 1, except that it was formulated as described above and L-menthol and the antiinflammatory were together added to the dissolved material.

Comparative Example 5

| | |
|---|---|
| styrene-isoprene-styrene block copolymer (Cariflex TR-1111) | 15.00 parts |
| high molecular weight polyisobutylene (Vistanex MM L-120) | 5.00 parts |
| rosin-based resin (Pinecrystal KE-311) | 37.00 parts |
| liquid paraffin | 23.00 parts |
| zinc stearate | 5.00 parts |
| ketoprofen | 5.00 parts |
| L-menthol | 10.00 parts |

A plaster was prepared similarly to Example 1, except that it was formulated as described above and L-menthol and the antiinflammatory were together added to the dissolved material.

Test Example 1

Medicament Release Test

A test for the medicament releasing-capabilities of the plasters produced in Examples 1 to 4 was carried out according to the rotating cylinder method described in the release test as prescribed in United state pharmacopoeia (USP) under the following conditions:
Test solution: distilled water
Solution temperature: 32±0.5° c.
The distance between the lower end of cylinder and the inner bottom surface of container: 12±2 mm
The number of revolutions: 50 rpm.

The results obtained are shown in Table 1 and FIG. 1. In FIG. 1, the horizontal axis represents the time after the start of test, while the vertical axis represents the release rate of the antiinflammatory.

As is apparent from the results shown in Table 1 and FIG. 1, the medicament release rates of the plasters of this invention as obtained in Examples 1 to 4 one hour later were 20-64% by mass; and those at three hours later were 40-93% by mass. It was thus confirmed that constantly high medicament releasing-capabilities are consistently maintained. Particularly, among those results, in the plasters of the invention as obtained in Examples 1 and 2, the medicament release rates one hour later were about 30-50% by mass and those three hours later were about 60-80% by mass. It was confirmed that they are especially excellent plasters in consideration of skin irritation, transdermal absorbability, duration etc.

TABLE 1

| | medicament release rate (% by mass) | |
|---|---|---|
| | one hour later | three hours later |
| Example 1 | 35.4 | 66.4 |
| Example 2 | 40.1 | 72.7 |
| Example 3 | 20.5 | 40.7 |
| Example 4 | 63.2 | 93.0 |

Test Example 2

Human Skin Affixing Test

The plasters produced in Examples 1, 2, 3 and 4 were punched out 5 cm×5 cm-square shapes and affixed to the inner sides of forearms of 10 healthy adults. Adhesion and pain upon peeling 12 hours later were evaluated. The evaluation results from the 10 subjects are shown in Table 2.

As is apparent from the results shown in Table 2, it was confirmed that the plasters of this invention were excellent in adhesion and pain upon peeling and that where zinc stearate was blended in a range of from 0.1 to 5% by mass, especially excellent adhesion was maintained with alleviated pain upon peeing.

TABLE 2

| | | Ex. 1 | Ex. 2 | Ex. 3 | Ex. 4 |
|---|---|---|---|---|---|
| adhesion 12 hours after affixing (the number of applicable subjects) | no peeling | 1 | 0 | 0 | 0 |
| | peeling only at end portions | 9 | 9 | 10 | 0 |
| | peeled portion <½ of the total | 0 | 1 | 0 | 3 |
| | peeled portion ≧½ of the total | 0 | 0 | 0 | 6 |
| | coming off | 0 | 0 | 0 | 1 |
| pain upon peeing 12 hours after affixing (the number of applicable subjects) | almost no pain felt | 10 | 9 | 0 | 10 |
| | a little pain felt | 0 | 1 | 0 | 0 |
| | pain felt | 0 | 0 | 3 | 0 |
| | strong pain felt | 0 | 0 | 7 | 0 |

Test Example 3

Human Skin Adhesive Strength Measurement

The plasters produced in Examples 1, 2, 3, and 4 were cut into small pieces (2 cm×2 cm) and they were affixed onto the skin of forearms of 10 healthy adults. Twelve hours after affixing, the peripheries of the plaster were fixed by a clip connected to a digital force gage. The digital force gage was raised at a constant rate and the plaster was retained without being peeled for a predetermined period while it was kept at 90° to the human skin. Force was then measured when peeled. The averages of the evaluation results for ten people are shown in Table 3. Numerical criteria for judgment are as follows: 100-200 g shows desirable adhesive strength; with less than that the adhesive strength is not sufficient and causes peeling upon affixing; and with above that the adhesive strength is too strong aid causes pain upon peeling.

As is apparent from the results shown in Table 3, it was confirmed that the plasters of this invention were excellent in adhesion and where zinc stearate was blended in a range of from 0.1 to 5% by mass, especially adequate adhesive strength was obtained

TABLE 3

| | Example 1 | Example 2 | Example 3 | Example 4 |
|---|---|---|---|---|
| adhesive strength at 12 hours after affixing (g) | 160 | 168 | 251 | 70 |

Test Example 4

Thermal Stability Test

The plasters produced in Examples 1, 2 and 6 and Comparative Examples 2, 3, 4 and 5 were punched into circles with 3 cm-diameter and they were placed in packaging materials sealed with aluminum polyethylene compound film. After storage at 40° c. for four weeks, the adhesive strength of each plaster was measured by the probe tack method (the device used: PROVE TACK TESTER). Measurements were repeated three times and the averages of the results obtained are shown in Table 4. During the probe tack test, observation was made as to whether exudation had appeared at the adhered part, and the results obtained are also shown in Table 4.

As is apparent from the results shown in Table 4, it was confirmed that the plasters of this invention were excellent in the thermal stability of the adhesive base and that where the high molecular weight polyisobutylene was blended in a range of from 3.6 to 12% by mass, plasticization of the adhesive base under the influence of heating as well as the exudation were fully prevented.

TABLE 4

| | probe tack measurements after storage (g) | condition of the adhered part after storage |
| --- | --- | --- |
| Example 1 | 70 | no exudation |
| Example 2 | 74 | no exudation |
| Example 6 | 79 | no exudation |
| Comparative Example 2 | 32 | exudation |
| Comparative Example 3 | 42 | no exudation |
| Comparative Example 4 | 29 | exudation |
| Comparative Example 5 | 39 | no exudation |

Test Example 5

Medicament Stability Test

The plasters produced in Examples 1 to 10 and Comparative Examples 1 to 5 were stored at 40° c. for six months, after which the medicament stability test was carried out. Specifically, the amounts of residual medicament and the amounts of esterified medicament in the stored plasters (adhesive preparations) were determined by liquid chromatography. Measurement was repeated three times, and the averages of the results obtained are shown in Table 5.

As is apparent from the results shown in table 5, it was confirmed that almost 100% of the antiinflammatory remained after storage in the plasters of this invention into which L-menthol had not been blended, while that about 5 to 15% of the antiinflammatory had been esterified after storage in the plasters which contain L-menthol and were produced in Comparative Examples 1 to 5.

TABLE 5

| | amount of residual medicament (% by mass) | content of esterified compound (% by mass as converted) |
| --- | --- | --- |
| Example 1 | 99.81 | 0 |
| Example 2 | 99.63 | 0 |
| Example 3 | 99.92 | 0 |
| Example 4 | 99.89 | 0 |
| Example 5 | 99.91 | 0 |
| Example 6 | 99.99 | 0 |
| Example 7 | 99.92 | 0 |
| Example 8 | 99.93 | 0 |
| Example 9 | 99.83 | 0 |
| Example 10 | 99.90 | 0 |
| Comparative Example 1 | 84.92 | 15.08 |
| Comparative Example 2 | 90.12 | 9.86 |
| Comparative Example 3 | 85.65 | 14.32 |
| Comparative Example 4 | 94.32 | 5.68 |
| Comparative Example 5 | 84.92 | 15.08 |

Test Example 6

Guinea Pig Skin Irritation Test

The plasters produced in Examples 1 and 2 and Comparative Examples 1 and 3 were cut into small pieces (2 cm×2 cm) and they were affixed onto the dorsal skin of neck of guinea pigs that had been shaven for 24 hours. The skin conditions at one hour after peeling were observed by the naked eyes. The results were evaluated according to the criteria described below, and the results obtained are shown in Table 6. The number of guinea pigs for experiment was set to be 10 animals per group. The positive ratio was calculated following the equation described below.

Positive ratio=(score×number of animals)/(maximum score×total number of animals)

(Evaluation Criteria)

| formation of erythema and scab | score |
| --- | --- |
| no change | 0 |
| very slight erythema | 1 |
| slight erythema | 2 |
| moderate to severe erythema | 3 |
| severe erythema in deep red and slight scab formation | 4 |

As is apparent from the results shown in Table 6, it was confirmed that while the plasters of this invention fully prevented the occurrence of harmful effects by skin irritation, the plasters produced in Comparative Examples 1 and 3 did not sufficiently prevent the occurrence of harmful effects by skin irritation.

TABLE 6

| | conditions of the skin (animal number per score with respect to erythema and scab formation) | | | | | total animals | positive ratio (%) |
| --- | --- | --- | --- | --- | --- | --- | --- |
| | 0 | 1 | 2 | 3 | 4 | | |
| Example 1 | 9 | 1 | 0 | 0 | 0 | 10 | 2.5 |
| Example 2 | 9 | 1 | 0 | 0 | 0 | 10 | 2.5 |

TABLE 6-continued

| | conditions of the skin (animal number per score with respect to erythema and scab formation) | | | | | total animals | positive ratio (%) |
|---|---|---|---|---|---|---|---|
| | 0 | 1 | 2 | 3 | 4 | | |
| Comparative Example 1 | 1 | 6 | 3 | 0 | 0 | 10 | 30.0 |
| Comparative Example 3 | 0 | 5 | 3 | 2 | 0 | 10 | 42.5 |

INDUSTRIAL APPLICABILITY

As described above, according to this invention, it will be possible to obtain an antiinflammatory-containing plaster that can consistently produce, over a long period of time, sufficient anti-inflammatory, analgesic effect by the antiinflammatory having a carboxyl group or a salt thereof without bringing harmful effects such as skin irritation and that is additionally excellent in its adhesion as well as in the stability of adhesive base with alleviated pain upon peeling, despite the fact that L-menthol is not blended therein. Accordingly, this invention is capable of providing an antiinflammatory-containing plaster useful as a drug (plaster for external application) that is intended for anti-inflammation and analgesia.

The invention claimed is:

1. A method of avoiding crystallization of an anti-inflammatory medicament in an anti-inflammatory-containing plaster having adhesion to skin, comprising:
providing a plaster consisting essentially of
5-40% by mass of a styrene-isoprene-styrene block copolymer,
1-25% by mass of a high molecular weight polyisobutylene having an average molecular weight of 50,000-200,000,
0.5-24% by mass of a low molecular weight polyisobutylene having an average molecular weight of 5,000-15,000,
3-50% by mass of a tackifier, 20-70% by mass of a plasticizer,
0.01-7% by mass of a dispersant selected from the group consisting of metal salts of fatty acid and aluminum hydroxide, the dispersant enhancing dispersibility of the styrene-isoprene-styrene block copolymer and the high molecular weight and low molecular weight-polyisobutylenes, and
0.1-8% by mass of an anti-inflammatory comprising a carboxyl group or a salt thereof as the anti-inflammatory medicament; and
storing the plaster,
wherein the anti-inflammatory-containing plaster does not contain L-menthol, and when the plaster is stored, the anti-inflammatory comprising a carboxyl group or a salt thereof does not undergo esterification.

2. The method according to claim 1, wherein the styrene-isoprene-styrene block copolymer is present in an amount of 8-35% by mass.

3. The method according to claim 1, wherein the high molecular weight polyisobutylene is present in an amount of 2-18% by mass.

4. The method according to claim 1, wherein the low molecular weight polyisobutylene is present in an amount of 1-20% by mass.

5. The method according to claim 1, wherein the tackifier is present in an amount of 4-40% by mass.

6. The method according to claim 1, wherein the plasticizer is present in an amount of 25-65% by mass.

7. The method according to claim 1, wherein the dispersant is present in an amount of 0.05-6% by mass.

8. The method according to claim 1, wherein the anti-inflammatory medicament is selected from the group consisting of ketoprofen, flurbiprofen and diclofenac.

9. The method according to claim 1, wherein the anti-inflammatory medicament is ketoprofen and is present in an amount of from 0.5-5.0% by mass.

* * * * *